(12) United States Patent
Sherman et al.

(10) Patent No.: US 7,708,946 B1
(45) Date of Patent: May 4, 2010

(54) DEVICE FOR PROTEIN DETECTING TESTS

(76) Inventors: Michael Sherman, 53 Charlotte Rd., Newton, MA (US) 02459; Yury Sherman, 511 Beech St., Roslindale, MA (US) 02131; Abram Botvinnik, 1196 Queen La., Apt. 4, West Chester, PA (US) 19382

( * ) Notice: Subject to any disclaimer, the term of this patent is extended or adjusted under 35 U.S.C. 154(b) by 36 days.

(21) Appl. No.: 12/291,647

(22) Filed: Nov. 12, 2008

Related U.S. Application Data

(63) Continuation-in-part of application No. 10/937,439, filed on Sep. 9, 2004, now abandoned, and a continuation-in-part of application No. 09/907,833, filed on Jul. 19, 2001, now abandoned.

(51) Int. Cl.
*G01N 21/00* (2006.01)

(52) U.S. Cl. .............................. 422/63; 422/58; 422/67; 422/99; 422/100; 422/103; 422/106; 422/110; 436/165; 436/180; 436/528; 436/808; 435/7.9; 435/7.92; 435/287.2; 435/287.3

(58) Field of Classification Search ................... 422/58, 422/63, 67, 99, 100, 103, 106, 110; 435/7.9, 435/7.92, 287.2, 287.3; 436/165, 180, 528, 436/808; 366/260
See application file for complete search history.

(56) References Cited

U.S. PATENT DOCUMENTS

| | | | |
|---|---|---|---|
| 3,850,580 A * | 11/1974 | Moore et al. .................... 422/99 |
| 4,029,470 A * | 6/1977 | Wilkins et al. ................ 8/94.11 |
| 4,859,419 A * | 8/1989 | Marks et al. .................... 422/56 |
| 4,895,706 A * | 1/1990 | Root et al. .................... 422/102 |
| 4,948,564 A * | 8/1990 | Root et al. .................... 422/101 |
| 5,190,666 A * | 3/1993 | Bisconte ....................... 210/744 |
| 5,346,303 A * | 9/1994 | Heinonen et al. ............ 366/208 |
| 5,529,756 A * | 6/1996 | Brennan ....................... 422/131 |
| 5,564,826 A * | 10/1996 | Neumann et al. ............ 366/219 |
| 5,567,595 A * | 10/1996 | Kok ............................ 435/7.92 |
| 5,674,006 A * | 10/1997 | Islam et al. .................. 366/239 |
| 6,083,761 A * | 7/2000 | Kedar et al. .................... 506/30 |
| 6,174,733 B1 * | 1/2001 | Chen ............................. 436/501 |
| 6,379,565 B1 * | 4/2002 | Guirguis et al. ............. 210/767 |
| 6,440,372 B1 * | 8/2002 | Pages .......................... 422/101 |
| 2002/0028159 A1 * | 3/2002 | Lebl et al. ...................... 422/99 |
| 2002/0048535 A1 * | 4/2002 | Weigl et al. .................. 422/100 |
| 2002/0064880 A1 * | 5/2002 | Merten et al. ................. 436/43 |
| 2003/0044322 A1 * | 3/2003 | Andersson et al. .......... 422/100 |

\* cited by examiner

*Primary Examiner*—Lyle A Alexander
*Assistant Examiner*—Dennis M White
(74) *Attorney, Agent, or Firm*—K. Gibner Lehmann

(57) ABSTRACT

A device for automation of biological and medical tests wherein test subjects or specimens that are placed in test vessels are subsequently treated by different liquid reagents, including: at least two test vessels of dimensions providing accommodation of specimens, a hydraulic gravity feeding system to deliver the liquid reagents into the two test vessels, a hydraulic gravity discharging system to remove waste liquid or spent reagents from the test vessels and directing them into an apparatus for accommodation of the such waste liquid or spent reagents, and a control system operating the device. A mechanical system is provided for agitating the test vessels.

20 Claims, 5 Drawing Sheets

DEVICE FOR PROTEIN DETECTING TESTS

CROSS REFERENCES TO RELATED APPLICATIONS

The present application is a continuation-in-part of, and claims the priority benefit, under 35 USC 119 or 120, of our prior U.S. application Ser. No. 09/907,833 filed Jul. 19, 2001, now abandoned; and the present application is also a continuation-in-part of, and claims the priority benefit, under 35 USC 119 or 120, of our prior U.S. application Ser. No. 10/937,439 filed Sep. 9, 2004, said application Ser. No. 10/937,439, now abandoned.

STATEMENT AS TO RIGHTS TO INVENTIONS MADE UNDER FEDERALLY SPONSORED RESEARCH AND DEVELOPMENT

Research and development of the present invention and application have not been Federally-sponsored, and no rights are given under any Federal program.

BACKGROUND OF THE INVENTION

1. Field of the Invention

The present invention relates to immunodetection generally, and more particularly to a novel device for protein detecting tests.

2. Description of the Related Art Including Information Disclosed Under 37 CFR 1.97-1.99

While the present invention is described in detail with reference to a device for Western blot tests, it will be understood that it is applicable as well to a family of the devices for similar tests.

Detection of proteins immobilized on various matrixes using immunological methods is a widespread procedure both in biomedical research areas and in clinics. A common example of such detection methods is what has become known as the Western blotting procedure, where proteins separated by polyacrylamide gel electrophoresis are transferred to an immobilizing matrix for immunodetection. Although conceptually simple, the process of detecting molecules of interest by immunological methods is a tedious and labor-intensive task, involving successive incubation with a series of reagents and washes.

To reduce the "hands-on" time requirements for immunodetection, several instruments have been developed, such as the Western Processor of Bio-Rad Laboratories, and the Hoefer Processor Plus of Amersham Pharmacia Biotech, that automate the time-consuming steps of these routine protocols. In the design of both devices, a rocker platform providing agitation of the blotting reagents and pumps for reagent delivery and discharging of test vessels are used. Pumping of the reagents determines the main drawback of the devices; its structural complexity increases dramatically as the number of test vessels and variability in primary and secondary antibodies increase. For this reason, the number of test vessels in both devices is limited currently by four, and the numbers of used primary and secondary antibodies in both devices are limited by one and one. This strongly limits the capacity of the devices and their abilities to make several tests with different antibodies simultaneously. With other protocols for immunodetection, FLISA or immunocytochemistry, only very expensive robots have been used for automation, and no specialized inexpensive devices for automation have been developed.

SUMMARY

Accordingly, the objects of the invention are considered to include at least some of the following: to provide a device for automation of biological and medical tests wherein test specimens placed in a test vessel are subsequently treated by different liquid reagents according to a test protocol.

Further, to provide such a device in which there are a number of gravity flow lines for reagents wherein the reagents are being automatically processed in compliance with predetermined test requirements, exemplified by their flow from feed containers to waste-accepting means.

Further: to provide such a device that includes a mechanical system including moveable test vessels which movement generates agitation of the reagents and test specimens placed therein, a hydraulic gravity feeding system delivering the reagents into the test vessels; a hydraulic gravity discharging system removing the reagents from the test vessels and directing them into containers for collecting spent reagents or a sewer system, and a control system operating the device.

Still further, to provide such a device in which the mechanical system provides agitation of the reagents inside the test vessels.

Still further: to provide such a device wherein the hydraulic gravity feeding system consists of a number of feeding containers placed above the test vessels, a measuring unit placed below the feeding containers but above the test vessels, and connecting tubes therefor.

Finally: to provide such a device in which valves located in the measuring unit regulate or operate the reagent feeding flows.

The hydraulic gravity discharging system comprises a number of the reagent flow lines, some of which are served for transportation of wasted primary antibodies into collecting containers for secondary usage, and others for transportation of other reagents to a sewer system.

Some of the reagent flow lines include valves located below the test vessels, which regulate or operate the reagent discharging flows, and tubes connecting the valves with the test vessels and the means for accommodation of waste reagents.

Preferably all tubes used in the feeding and the discharging systems in combination with valves are made of resilient, or elastic materials having good shape memory and which are nontacky under long-term pressure.

The use of resilient, flexible tubes has two distinct advantages: One is that where the tubes are attached to the test vessels, there is required to be a certain amount of slack to the tubes, to permit the test vessels to be agitated. In the absence of such flexible tubes, rigid connections would have to be made, which would inhibit the required agitation of the test vessels.

Next, where laboratory space is limited, the arrangement provided by the invention utilizes components that are disposed mostly one above the other, as opposed to a side-by-side disposition. Accordingly, space requirements are accommodated, since the present invention does not use up valuable table space as in a side-by-side arrangement of the components of the test device. Moreover, the flexibility of the tubes enables limited shifting of the various components, into optimal positions, or into positions dictated by the available space in the laboratory.

The device is advantageously operated by programmable control means.

Other objects of the present invention, as well as particular features, elements, and advantages thereof, will be elucidated in, or be apparent from, the following description and the accompanying drawing figures.

The present invention, as embodied by the main claim appended hereto, provides:

In the field of performing immunoblot tests, DNA blots and RNA blots, on biological materials that are positioned in equipment that subjects the material to predetermined tests which involve reagent-type liquids that flow through piping in the form of test processing lines according to predetermined test protocols, and wherein such tests produce results that are derived from reaction of said reagent-type liquids that flow through the piping, and wherein there is a device for carrying out specific biological and/or medical tests in a laboratory facility, and wherein said tests involve specific test specimens that are treated by different liquid reagents, said device comprising in combination:

means providing an upright support for placement on a bench or floor of the laboratory facility, at least two test vessels movably connected with said support and arranged to carry said test specimens, respectively, said test vessels being open to the air at their tops and being disposed at a first, predetermined height (h1) above said floor, each of said test vessels having two inlets for acceptance of said liquid reagents into the respective test vessel, and each of said test vessels having two outlets for removing said spent reagent and said waste material from said respective test vessel, a gravity-operated feed system comprising a reagent-feed container and a measuring unit connected thereto by a group of tubes constituted of flexible substance, said reagent-feed container being disposed at a second predetermined height (h2) above said floor, said second predetermined height being greater than said first predetermined height of said test vessels, all of said group of tubes being separated from one another to prevent cross-transferance or contamination between liquids carried thereby, said measuring unit being connected to said test vessels by another group of tubes constituted of flexible substance, said measuring unit being disposed at a third predetermined height (h3) above said floor, said third predetermined height being between said first and second predetermined heights, whereby liquid reagent/water from said reagent-feed container can selectively flow, solely under the force of gravity and without pumps of any kind, into the measuring unit, and subsequently from the measuring unit into said test vessels, respectively, all without the use of pumps of any type and without cross-transference or contamination of the liquid being carried in said another group of tubes, a discharge unit connected with said test vessels by yet another group of tubes, said discharge unit being located at a fourth predetermined height (h4) with respect to said floor, said fourth predetermined height being less than said first predetermined height (h1) of said test vessels, whereby spent reagent and waste material from said test vessels can selectively flow, solely under the force of gravity and without the use of pumps of any kind, into said discharge unit to be suitably discarded thereby and without cross-transference or contamination of the liquid being carried in said immediately preceding group of tubes, motorized means for agitating the test vessels by providing for reciprocating movement to said test vessels and mixing through the test specimens therein, and a control system regulating flow of reagent between said reagent-feed container and said measuring unit, between said measuring unit and said test vessels, and between said test vessels and said discharge unit, according to a predetermined time schedule constituted as part of said control system, said control system flow regulation being fully capable of either simultaneous or individual operation of said flows of reagent/water out of said container, into and out of said measuring unit, through all of said tubes, through said test vessels, and into said discharge unit.

The invention also provides a device for automation of biological and medical tests in a laboratory facility, wherein test specimens are treated by different liquid reagents, said device comprising in combination:

a) an upright support for placement on a laboratory bench or on the floor of a laboratory facility, b) two test vessels movable connected with said support and arranged to carry said test specimens, respectively, said test vessels being disposed at a first, predetermined height above said floor, c) a gravity-operated feed system comprising a reagent-feed container and a measuring unit connected thereto by a group of tubes constituted of flexible substance, said reagent-feed container being disposed at a second predetermined height above said floor, said second predetermined height being greater than said first predetermined height of said test vessels, said measuring unit being connected to said test vessels by another group of tubes constituted of flexible substance, said measuring unit being disposed at a third predetermined height above said floor, said third predetermined height being between said first and second predetermined heights, whereby liquid reagent from said reagent-feed container can selectively flow, solely under the force of gravity, into the measuring unit, and subsequently from the measuring unit into said test vessels, respectively, d) a discharge unit connected with said test vessels by yet another group of tubes, said discharge unit being located at a fourth predetermined height with respect to said floor, said fourth predetermined height being less than said first predetermined height of said test vessels, whereby spent reagent and waste material from said test vessels can selectively flow, solely under the force of gravity, into said discharge unit to be suitably discarded thereby, e) motorized means for agitating the test vessels by providing for reciprocating movement to said test vessels and mixing through the test specimens therein, and f) a control system regulating flow of reagent between said reagent-feed container and said measuring unit, and between said measuring unit and said test vessels, according to a predetermined time schedule constituted as part of said control system.

Other features and advantages will hereinafter appear.

BRIEF DESCRIPTION OF THE DRAWINGS

Understanding of the present invention and the various aspects thereof will be facilitated by reference to the accompanying drawing figures, provided for purposes of illustration only and not intended to define the scope of the invention, in which.

Figure 1:
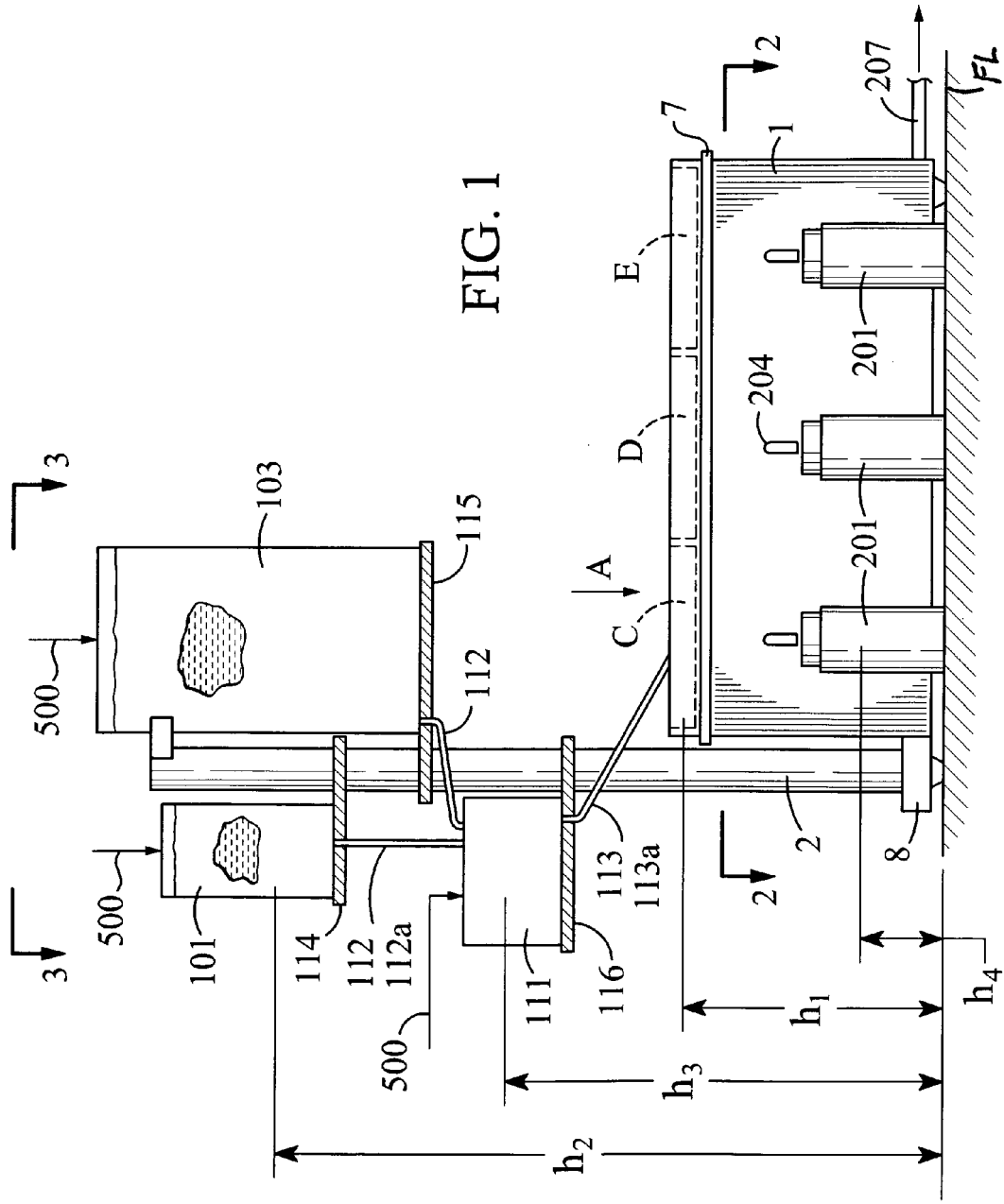
FIG. 1 is a fragmentary front view of a device constructed according to the present invention.

DESCRIPTION OF THE PREFERRED EMBODIMENT AND INVENTORS' BEST MODE OF CARRYING OUT THE INVENTION

Reference should now be made to the drawing figures on which similar or identical elements are given consistent identifying numerals throughout the various figures thereof, and on which parenthetical references to figure numbers direct the reader to the view(s) on which the element(s) being described is (are) best seen, although the element(s) may be seen on other figures also.

The invention is related to devices for the automation of biological and medical tests wherein a test specimen placed in a test vessel is subsequently treated by different liquid reagents according to a test protocol. For example, it can be a device for Western blot tests wherein gel matrixes placed in the test vessels are treated by a number of reagents. During the tests, the reagents have to be dosed, then delivered into the test vessels, agitated in the test vessels, removed from the test vessels, and directed to reagent collecting containers or to a sewer system.

The mechanical principle of this invention is the provision of a number of gravity flow lines of the reagents wherein the reagents are automatically processed according to a predetermined subsequence on their way from feeding containers to the waste-accepting means.

The description of the invention is made with an example of a device for the automation of the Western blot tests. The device performance covers typical Western blot test protocols including the following treatments of the tested gel matrixes:
  a. Blocking
  b. Washing #1
  c. Processing of the gel matrixes with primary antibodies
  d. Washing #2
  e. Processing of the gel matrixes with secondary antibodies
  f. Washing #3

The device can process up to six matrixes simultaneously using up to six different primary antibodies and up to two different secondary antibodies.

Referring to the drawings in detail, in FIGS. 1-9 a device for Western blot tests is shown in the preferred embodiment. The device includes two main parts: a body 1 and an upright rack support 2. The body, in turn, includes a housing, a base, a block of six test vessels, a mechanical system for reciprocating movement of the test vessels, a hydraulic gravity feeding system for measuring, distributing, and delivering the reagents into the test vessels, a hydraulic gravity discharging system for removing waste reagents from the test vessels and transporting them to the waste primary antibody containers and sewer system, and a control system for operating the device.

Rack support 2 supports two main elements of the hydraulic gravity feeding system on the floor of the laboratory facility, such floor being designated FL in FIG. 1, said main elements of the hydraulic gravity feeding system being: the feeding containers and the reagent measuring unit.

Figure 2:
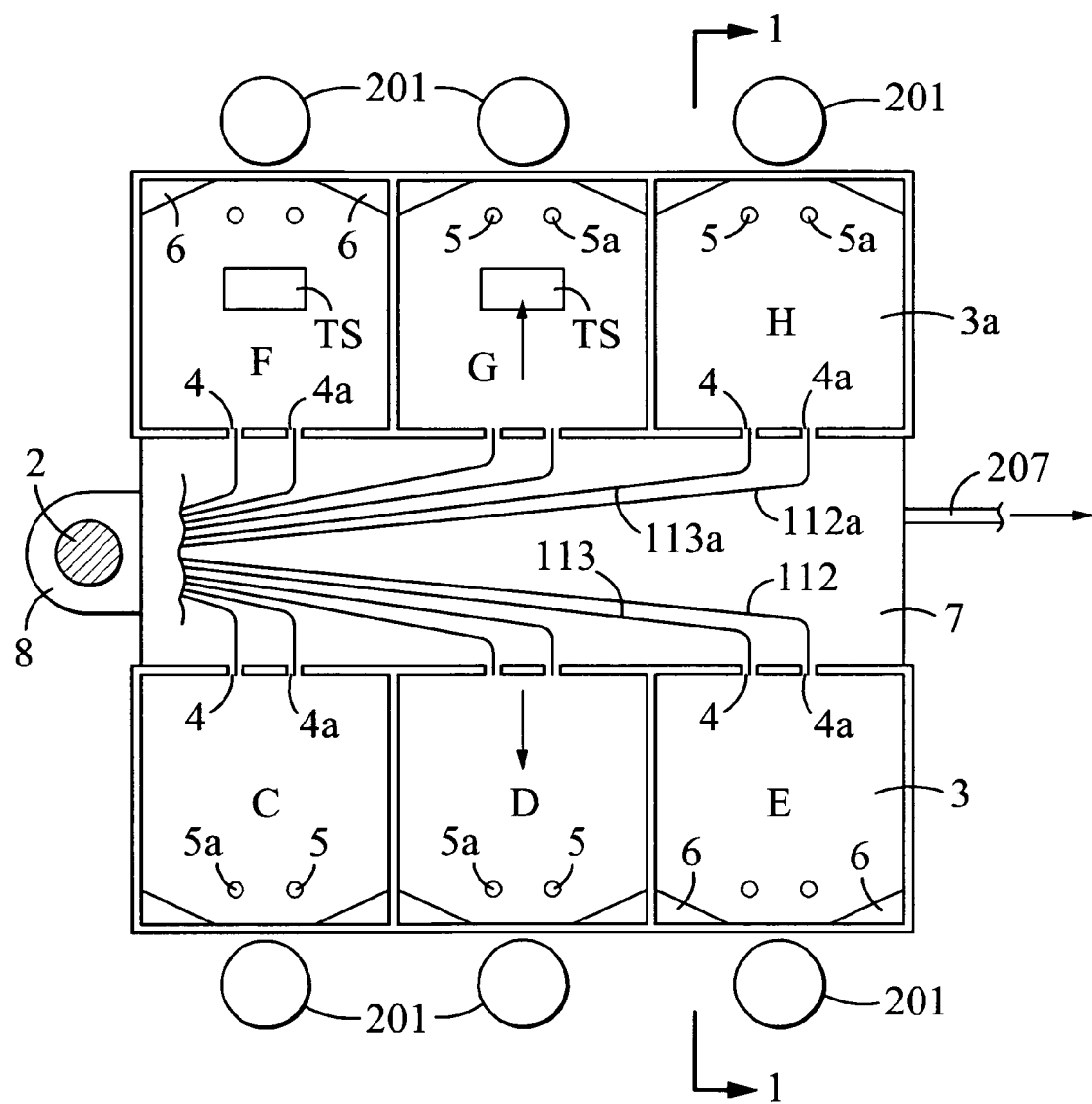
FIG. 2 is a top plan view taken along arrow A shown in FIG. 1.

FIGS. 1 and 2 show test vessels C, D, E, F, G and H, where the gel matrixes or test specimens are tested. They are rectangular boxes combined into two sets 3 and 3a of three test vessels each (C, D, E, and H, G, F). Each set can be substituted with one or two test vessels of larger sizes. The test vessels have inlets 4 for the delivery of primary antibodies and one or more inlets 4a for the delivery of other reagents into the test vessels. The test vessels also have outlets 5 and 5a for discharging from the test vessels, waste primary antibodies and other reagents, accordingly. Typical test specimens TS, FIG. 2, are indicated in two of the test vessels. To accelerate the discharging process, the test vessels are each inclined off the device's centerline, as shown by the arrows in FIG. 2, and each has two corner triangles 6 directing reagent flows to the outlets. A horizontal plate 7 supports the test vessels.

Agitation of the reagents inside the test vessels during the tests may be achieved by the horizontal reciprocating movement of the test vessels that generates a wave-like movement of the reagents placed inside. Accordingly, plate 7 is supported by flat vertical springs 9. The upper ends of the springs are affixed to the plate and their lower ends are affixed to the base of the device. When the applied horizontal forces displace the plate about the base, the spring forces of opposite direction are generated, and when the plate is released from the applied forces it returns to its original position. By cyclical displacements and releases, the plate receives the required reciprocating movement.

Figure 4:
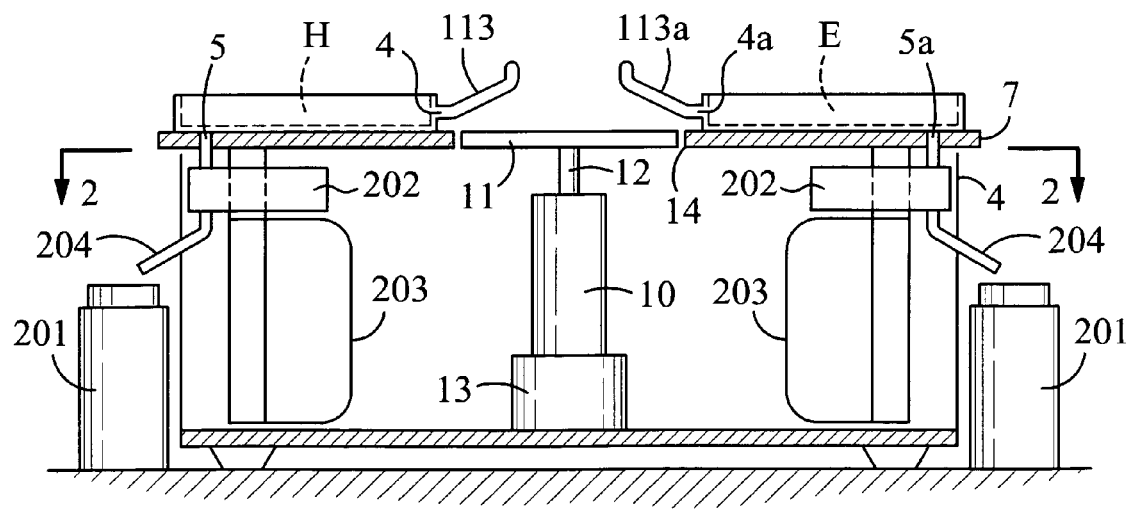
FIG. 4 is a cross sectional, side elevational view of the device taken on line 1-1 of FIG. 2.

As an instrument for plate displacements, an electric motor 10 supported by base 13, having shaft 12 and eccentric 11 affixed to the shaft, is used (FIG. 4). The eccentric, engaged with extensions 14 of plate 7, pushes and releases the plate when the motor is rotated. By this way, the reciprocating movement of the plates and the desirable wave-like movement of the reagents inside the test vessels are provided.

Figure 3:
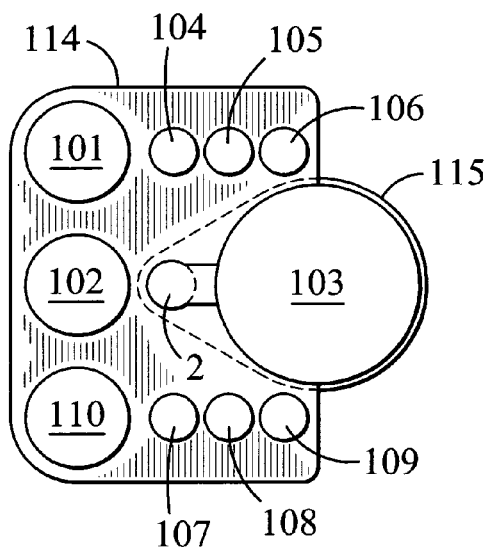
FIG. 3 is a fragmentary top view of the device showing reagent-feeding containers.

In accordance with the invention, the hydraulic gravity feeding system comprises of a number of feeding containers 101-110, all disposed at a height h2 above the floor, indicated FL in FIG. 1, a measuring unit 111 disposed at a height h3 placed below the feeding containers, but above the test vessels, which latter are at a height h1 in FIG. 1, and connecting tubes 112, 112a and 113 connecting the unit with the feeding containers and the test vessels (FIGS. 1, 3 and 4).

Plates 114 and 115 supporting the feeding containers and plate 116 supporting the measuring unit are attached to the rack 2. For removing the reagents out of the containers, each of them has an opening at its bottom. The containers are filled with the reagents manually, by the operator, in preparation of the device for the tests.

Figure 6:
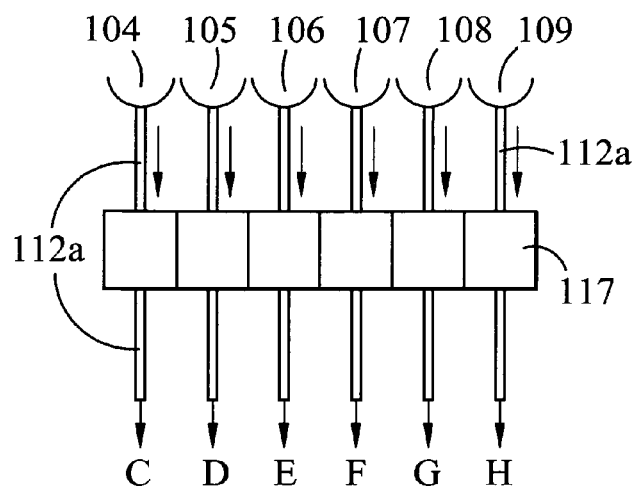
FIG. 6 is a schematic side elevational view of the primary antibody feed tubes.

The gravity flow feeding lines of the reagents—a system of tubes and mechanisms between the feeding container and the test vessels—are of the following structure:

Primary antibody lines: The device includes six lines that supply a number of test vessels and, accordingly, supports tests that may be performed simultaneously using different primary antibodies. To avoid cross-contamination each feeding container is connected to only one test vessel by a separate line or tube. Accordingly, each line consists of a controlling valve 117 and tube 112a connecting one of the feeding containers 104-109 to one of the test vessels C-H (FIG. 6). The valve is of the pinch type, normally closed, and located inside the measuring unit 111. When closed, the valve provides a watertight shutoff of the respective tube 112a. When opened, the valve causes the release of primary antibodies that flow into the test vessel. All primary antibody lines work simultaneously so that one valve structure 117 can serve several tubes.

Other reagent lines: The lines altogether are a mechanical system providing measurement of the reagents, and their delivery to the test vessels. As the number of used test vessels for any particular test may be different from another test, distribution of other reagents among the test vessels is an additional function performed by this system.

Figure 7:
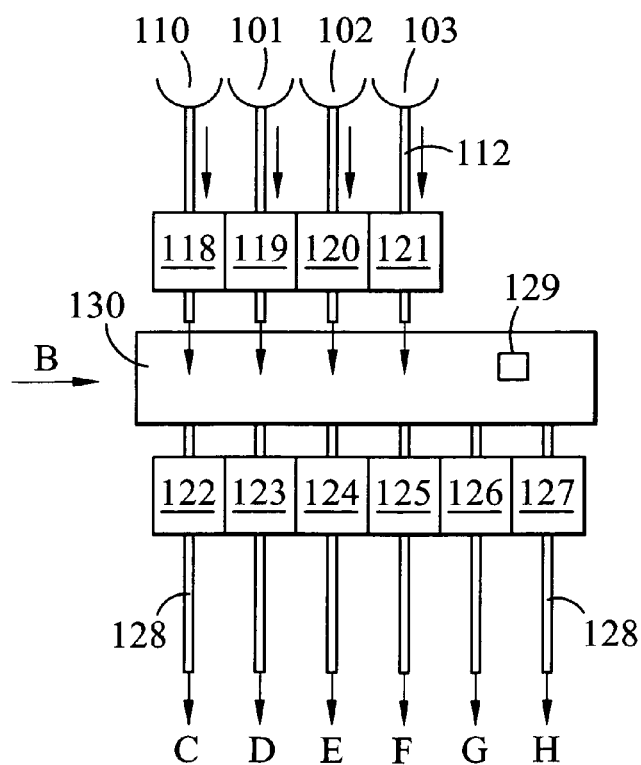
FIG. 7 is a schematic side elevational view of the other reagent feed tubes.
Figure 8:
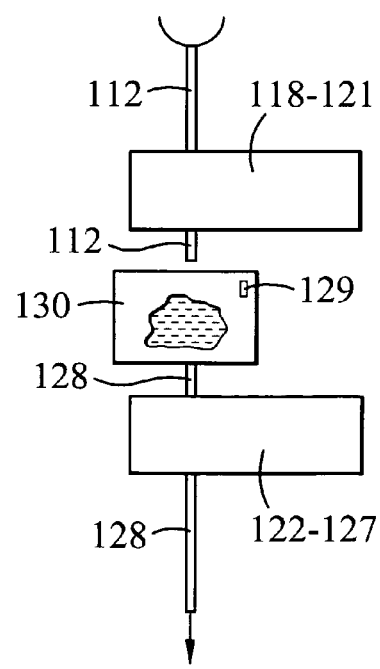
FIG. 8 is a side elevational view taken along arrow B of the schematic view shown in FIG. 7.

The system for the other reagent lines includes four other tubes 112 connecting feeding containers for blocking reagent, washer, and two secondary antibodies (101-103 and 110), with a measuring unit 130 (FIGS. 7 and 8). Four inlet valves 118-121 are installed along the tubes 112, one for each tube. The valves control delivery of the reagents to the measuring unit 130.

The system also includes six tubes 128 connecting measuring unit 130 with the test vessels—one tube for each test vessel C-H. Valves 122-127 are installed along the tubes 128 below measuring unit 130, one valve for each tube. The valves control distribution and delivery of the regents to the test vessels according to the test protocol. The valves are of the pinch type, normally closed, and located inside the measuring unit 111. When closed, they provide a watertight shutoff of tubes 128. When opened, the valves release the reagents that then flow into the test vessels.

Dosing of the reagents is performed in measuring unit 130. In the described embodiment, one dose of one reagent is measured at one time. Accordingly, delivery of the reagents into the test vessels is made consequently, one by one. Measuring unit may also be arranged such that more than one dose of a reagent may be measured and fed to more than one test vessel in a simultaneous manner.

To prepare the dose, one of the valves 118-121 is opened and the reagent flows into the measuring unit. The level of the reagent in the measuring unit is used as a volumetric measure of the reagent collected therein. However, usage of other methods of measuring of liquid inside a vessel is not excluded. When the necessary dose is prepared, means 129 detects this and sends an electrical signal to the control system of the device. The system closes the valve and thus, stops the flow of the reagent into the measuring unit. Then, one of the valves 122-127 is opened and the reagent flows from the measuring unit 130 into a proper vessel.

To accelerate the process and to increase the reliability of the reagent that flows through the feeding system, compressed air can be supplied through lines 500, to the measuring unit and the feeding containers. The additional pressure quickly forces the agents out of the various tubes.

Figure 5:
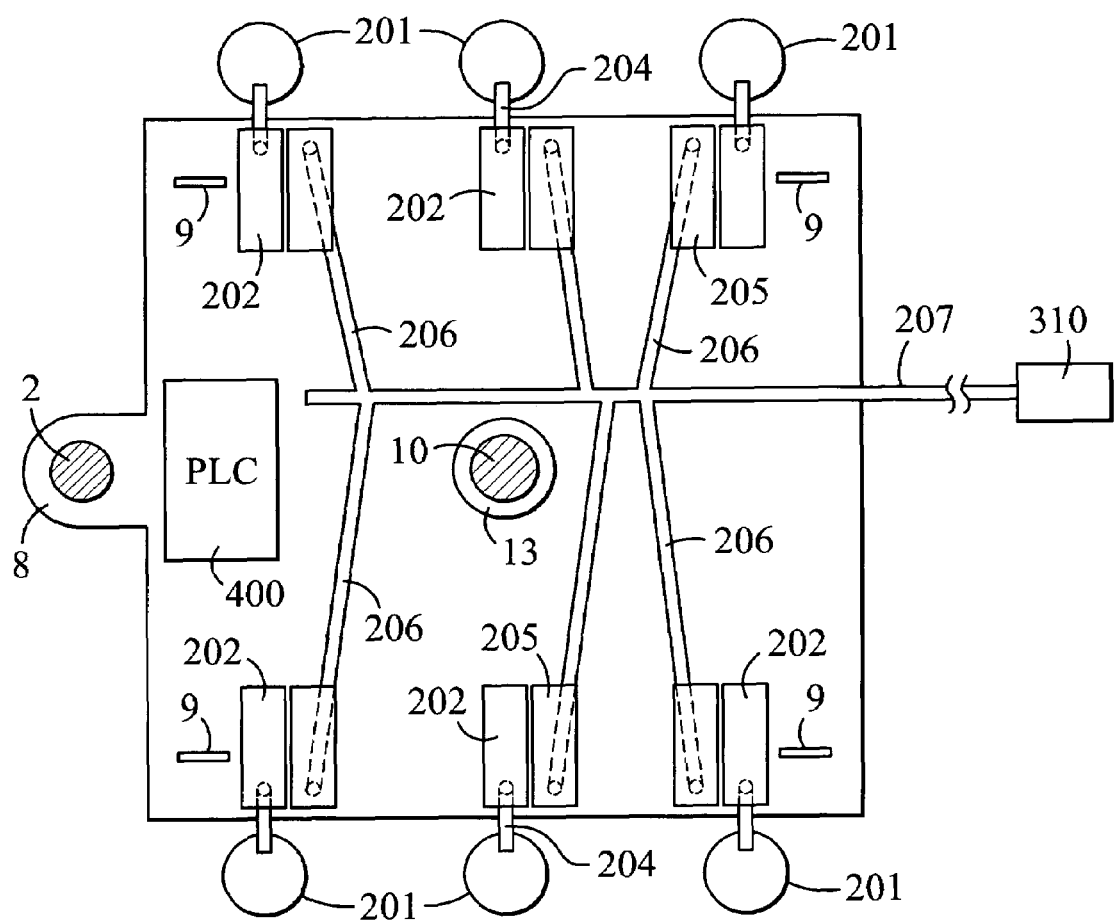
FIG. 5 is a cross sectional view of the device along the line 2-2 of FIG. 1.

The hydraulic gravity discharging system includes twelve tubes, six for transporting the waste primary antibodies into collecting containers 201 for secondary usage, and six for transporting other waste reagents from test vessels into manifold 207 and then to a sewer system 310 (FIG. 5).

Each of the discharging lines for the waste primary antibodies consists of a tube 204 connecting one of the test vessels C-H to one of the containers 201, and valves 202. The valves are required for operation of transportation of the waste primary antibodies to containers 201 according to a test protocol. The valves 202 are of a pinch type, normally closed, and located under the test vessels but above containers 201.

In accordance with the invention, the container 101 is disposed above the level or height h1 of the test vessels, such that gravity can be utilized to flow reagent from container 101 downwardly through measuring unit 111 which latter is shown as being at a height h3, and thereafter to the level of the test vessels, this level being designated in FIG. 1 by the indicia h1. Further by the invention, the test vessels at height h1 are above the level of the discharge containers 201, located at height h4, such that gravity can again be utilized to draw spent reagent or waste material from the twelve (12) test vessel outlets 5 or 5A, FIG. 2.

Returning to the discharging lines, when the valves 202 are closed, they provide an airtight shutoff of tubes 204, FIGS. 1 and 4. When opened, the valves release the waste primary antibodies that flow into containers 201. Preferably all waste primary antibody lines work simultaneously, so that one valve set 202 can operate several tubes.

Each of the discharging lines for the waste associated with the other reagents, consists of a tube 206 connecting one of the test vessels C-H to manifold 207, transporting the reagents to the sewer system 310 (FIG. 5), and a valve 205. The valve operates to transport the waste associated with the other reagents to the sewer system 310 according to a test protocol. The valves are of a pinch type, normally closed, and located under the test vessels and above the manifold 207. Support 203 supports discharging valves 202 and 205. When closed, the valves provide an airtight shutoff of the tubes 206. When opened, the valves release the other reagents that then flow into the manifold and then to the sewer system. All waste from the said other reagent lines work simultaneously, so that one valve set 205 can serve several tubes.

Figure 9:
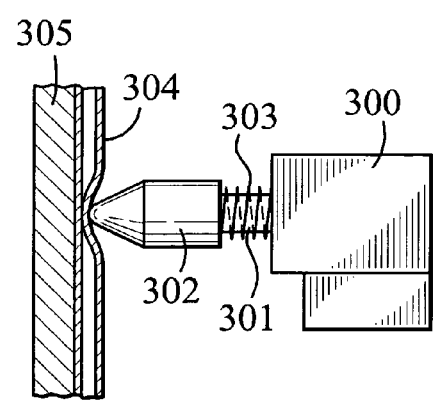
FIG. 9 is a side elevational view of the structure of the valves used for the device.

All valves used in the device are preferably of the structure shown in FIG. 9. Each valve may consist of a solenoid 300 having a plunger 301 with a mouthpiece 302. An extension spring 303 set between the solenoid frame and the mouthpiece pushes the plunger from within the solenoid. A tube 304 wherein a reagent flows is located across the mouthpiece. There is a wall support 305 preventing lateral displacement of the tube under mouthpiece pressure. Distance between the tube and the mouthpiece, and strength of spring 303 have to provide the lateral force well enough for airtight shutoff of the tube when the valve is switched off. When the valve is switched on, the plunger suppresses the spring and the lateral force is removed.

All tubes used in the hydraulic feeding and discharging systems are preferably made of resilient or elastic materials having good shape memory characteristic, and are nontacky under long-term pressure.

In this description, a Programmable Logic Controller (PLC) 400, FIG. 5, operates and controls the various functions. The main operational function of the PLC is to switch on and off, the valves controlling reagent feeding and test vessel discharging lines in compliance with time delays determined by a particular test protocol. At the same time, any appropriate systems for programmable controlling of technological processes can also be used.

In the embodiments of the present invention described above, it will be recognized that individual elements and/or features thereof are not necessarily limited to a particular embodiment but, where applicable, are interchangeable and can be used in any selected embodiment even though such may not be specifically shown.

Terms such as "upper", "lower", "inner", "outer", "inwardly", "outwardly", "vertical", "horizontal", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

Each and every one of the appended claims defines an aspect of the invention which is separate and distinct from all others, and accordingly it is intended that each claim be treated as such in any determination of novelty or validity.

Variations and modifications are possible without departing from the spirit of the invention.

The embodiments of the invention in which an exclusive property or privilege is claimed are defined as follows:

1. In the field of performing immunoblot tests, DNA blots and RNA blots, on biological materials that are positioned in equipment that subjects the material to predetermined tests which involve reagent-type liquids that flow through piping in the form of test processing lines according to predetermined test protocols, and wherein such tests produce results that are derived from reaction of said reagent-type liquids that flow through the piping, and wherein there is a device for carrying out specific biological and/or medical tests in a laboratory facility, and wherein said tests involve specific test specimens that are treated by different liquid reagents, said device comprising in combination:
   a) means providing an upright support for placement on a bench or floor of the laboratory facility,
   b) at least two test vessels movably connected with said support and arranged to carry said test specimens, respectively, said test vessels being open to the air at their tops and being disposed at a first, predetermined height (h1) above said floor, each of said test vessels having two inlets for acceptance of said liquid reagents into the respective test vessel, and each of said test vessels having two outlets for removing said spent reagent and said waste material from said respective test vessel,
   c) a gravity-operated feed system comprising a reagent-feed container and a measuring unit connected thereto by a group of tubes constituted of flexible substance, said reagent-feed container being disposed at a second predetermined height (h2) above said floor, said second predetermined height being greater than said first predetermined height of said test vessels, all of said first group of tubes being separated from one another to prevent cross-transferance or contamination between liquids carried thereby, said measuring unit being connected to said test vessels by another group of tubes constituted of flexible substance, said measuring unit being disposed at a third predetermined height (h3) above said floor, said third predetermined height being between said first and second predetermined heights, whereby liquid reagent/water from said reagent-feed container can selectively flow, solely under the force of gravity and without pumps of any kind, into the measuring unit, and subsequently from the measuring unit into said test vessels, respectively, all without the use of pumps of any type and without cross-transferance or contamination of the liquid being carried in said another group of tubes,
   d) a discharge unit connected with said test vessels by yet another group of tubes, said discharge unit being located at a fourth predetermined height (h4) with respect to said floor, said fourth predetermined height being less than said first predetermined height (h1) of said test vessels, whereby spent reagent and waste material from said test vessels can selectively flow, solely under the force of gravity and without the use of pumps of any kind, into said discharge unit to be suitably discarded thereby and without cross-transferance or contamination of the liquid being carried in said immediately preceding group of tubes,
   e) motorized means for agitating the test vessels by providing for reciprocating movement to said test vessels and mixing the test specimens therein, and
   f) a control system regulating flow of reagent between said reagent-feed container and said measuring unit, between said measuring unit and said test vessels, and between said test vessels and said discharge unit, according to a predetermined time schedule constituted as part of said control system, said control system flow regulation being fully capable of either simultaneous or individual operation of said flows of reagent/water out of said container, into and out of said measuring unit, through all of said tubes, through said test vessels, and into said discharge unit.

2. The invention as set forth in claim 1, and further including:
   a) automatically-operable valves placed in series with said first-mentioned group of tubes, and in series with said other groups of tubes, respectively.

3. The invention as set forth in claim 2, wherein:
   a) one of said valves is disposed in series with one tube of the group of tubes that extends from the reagent-feed container to the measuring unit, and
   b) another of said valves is disposed in series with a tube of said other group of tubes that extends from the measuring unit to the test vessels.

4. The invention as set forth in claim 3, wherein:
   a) said one valve and said other valve provide a watertight shutoff of each of said tubes, respectively.

5. The invention as set forth in claim 1, wherein:
   a) said first group of tubes and all of said other groups of tubes are made of elastic materials having good memory shape characteristic, and are characterized by non-tackiness under long-term compression and de-compression.

6. The invention as set forth in claim 1, wherein:
   a) said measuring unit has means for generating a signal when a predetermined quantity of said liquid reagent/water is collected from said reagent-feed container, and is ready to be released to one of said test vessels.

7. The invention as set forth in claim 2, wherein:
   a) said control system transmits signals to said valves, to open or close them at predetermined times, corresponding to desired release of reagent/water from said reagent-feed container and through said measuring unit.

8. The invention as set forth in claim 1, wherein:
   a) said discharge unit empties spent reagent and waste material into a waste container or into a sewer.

9. The invention as set forth in claim 1, wherein:
   a) said test vessels are capable of being inclined with respect to the horizontal and toward their outlets, respectively, thereby to assist in emptying the test vessels.

10. The invention as set forth in claim 1, wherein:
    a) said test vessels have angled corners respectively, directing waste reagent toward their outlets, respectively.

11. The invention as set forth in claim 1, wherein:
    a) said motorized means and reciprocating arrangement for the test vessels, includes springs engaging said test vessels and providing agitating, shaking movements thereto, as determined by said control system.

12. The invention as set forth in claim 11, wherein:
    a) said motorized means comprises an electric motor with an eccentric roller attached to its shaft, said roller being engaged with said springs, and wherein rotation of said eccentric roller displaces said springs, resulting in said agitating, shaking movements.

13. The invention as set forth in claim 1, wherein:
a) said motorized means is under the guidance of the control system, and is scheduled thereby to effect the reciprocating movements according to a schedule that is part of the control system.

14. The invention as set forth in claim 1, and further including:
a) a support plate interposed between the motorized means and the test vessels, said test vessels resting on said support plate, and
b) said motorized means directly agitating said support plate at times determined by the control means.

15. In the field of performing immunoblot tests, DNA blots and RNA blots, on biological materials that are positioned in equipment that subjects the material to predetermined tests which involve reagent-type liquids that flow through piping in the form of test processing lines according to predetermined test protocols, and wherein such tests produce results that are derived from reaction of said reagent-type liquids that flow through the piping, and wherein there is a device for carrying out specific biological and/or medical tests in a laboratory facility, and wherein said tests involve specific test specimens that are treated by different liquid reagents, said device comprising in combination:
a) means providing an upright support member, for placement on a bench or floor of the laboratory facility,
b) at least two test vessels movably connected with said support and arranged to carry said test specimens, respectively, said test vessels being open to the air at their tops and being disposed at a first, predetermined height (h1) above said floor, each of said test vessels having two inlets for acceptance of said liquid reagents into the respective test vessel, and each of said test vessels having two outlets for removing said spent reagent and said waste material from said respective test vessel,
c) a gravity-operated feed system comprising a reagent-feed container and a measuring unit connected thereto by a first group of tubes constituted of flexible substance, said reagent-feed container being disposed at a second predetermined height (h2) above said floor, said second predetermined height being greater than said first predetermined height of said test vessels, all of said first group of tubes being separated from one another to prevent cross-transference or contamination between liquids carried thereby, said measuring unit being connected to said test vessels by a second group of tubes constituted of flexible substance, said measuring unit being disposed at a third predetermined height (h3) above said floor, said third predetermined height being between said first and second predetermined heights, whereby liquid reagent/water from said reagent-feed container can selectively flow, solely under the force of gravity and without pumps of any type, through said first group of tubes and into the measuring unit, and subsequently flow through said second group of tubes, from the measuring unit into said test vessels, respectively, all without the use of pumps of any type and without cross-transference or contamination of the liquid being carried in said second group of tubes,
d) a discharge unit connected with said test vessels by yet another group of tubes constituted of flexible substance, said discharge unit being located at a fourth predetermined height (h4) with respect to said floor, said fourth predetermined height being less than said first predetermined height (h1) of said test vessels, whereby spent reagent and waste material from said test vessels can selectively flow, solely under the force of gravity and without the use of pumps of any kind, into said discharge unit to be either suitably discarded thereby, or recovered for use as recycled liquid reagent, all without cross-transference or contamination of the liquid being carried in said immediately preceding group of tubes,
e) said gravity-operated feed system further comprising a second reagent-feed container, said measuring unit being connected thereto by still another group of tubes constituted of flexible substance, said second reagent-feed container being disposed physically above the position of said test vessels, all of said immediately preceding group of tubes being separated from one another to prevent cross-transferance or contamination between liquids carried thereby, said measuring unit being connected to said test vessels by a still another group of tubes constituted of flexible substance, said measuring unit being disposed above the test vessels but below the second reagent-feed container, whereby liquid reagent/water from said second reagent-feed container can selectively flow, solely under the force of gravity and without pumps of any type, through said other group of tubes and into the measuring unit, and subsequently flow through said still another group of tubes, from the measuring unit into said test vessels, respectively, and out of said test vessels and into said discharge unit, all without the use of pumps of any type and without cross-transferance or contamination of the liquid being carried in any of said tubes,
f) motorized means for agitating the test vessels by providing for reciprocating movement to said test vessels and shaking of the test specimens therein, and
g) a control system regulating flow of reagent between said reagent-feed containers and said measuring unit, between said measuring unit and said test vessels, and between said test vessels and said discharge unit, according to predetermined time schedules constituted as part of said control system, said control system flow regulation being fully capable of either simultaneous or individual operation of said flows of reagent/water from said containers, into and out of said measuring unit, through said tubes, into and out of said test vessels, and into said discharge unit.

16. The invention as set forth in claim 15, wherein:
a) the motorized means is under the guidance of the control system, and operates to agitate the test vessels at predetermined times.

17. The invention as set forth in claim 16, and further including:
a) a support plate interposed between the motorized means and the test vessels, said test vessels resting on said support plate, and
b) said motorized means directly agitating said support plate at said predetermined times determined by the control means.

18. The invention as set forth in claim 17, and further including:
a) spring members interposed between said motorized means and said support plate, to transmit said agitation.

19. A device for automation of biological and medical tests in a laboratory facility, wherein test specimens are treated by different liquid reagents, said device comprising in combination:
a) an upright support for placement on a laboratory bench or on the floor of a laboratory facility, b) two test vessels movably connected with said support and arranged to carry said test specimens, respectively, said test vessels being disposed at a first, predetermined height above said floor, c) a gravity-operated feed system comprising a reagent-feed container and a measuring unit connected thereto by a group of tubes constituted of flexible substance, said reagent-feed container being disposed at a second predetermined height above said floor, said second predetermined height being greater than said first predetermined height of said test vessels, said measuring unit being connected to said test vessels by another group of tubes constituted of flexible substance, said measuring unit being disposed at a third predetermined height above said floor, said third predetermined height being between said first and second predetermined heights, whereby liquid reagent from said reagent-feed container can selectively flow, solely under the force of gravity, into the measuring unit, and subsequently from the measuring unit into said test vessels, respectively, d) a discharge unit connected with said test vessels by yet another group of tubes, said discharge unit being located at a fourth predetermined height with respect to said floor, said fourth predetermined height being less than said first predetermined height of said test vessels, whereby spent reagent and waste material from said test vessels can selectively flow, solely under the force of gravity, into said discharge unit to be suitably discarded thereby, e) motorized means for agitating the test vessels by providing for reciprocating movement to said test vessels and shaking of the test specimens therein, and f) a control system regulating flow of reagent between said reagent-feed container and said measuring unit, and between said measuring unit and said test vessels, according to a predetermined time schedule constituted as part of said control system.

20. The invention as set forth in claim 19, wherein:

a) said control system has the capacity to operate substantially in an automated fashion, to synchronize the flow of reagent from said reagent-feed container, through said measuring unit, through said test vessels, and into said discharge unit.

\* \* \* \* \*